US007371734B2

(12) United States Patent
Phillips et al.

(10) Patent No.: US 7,371,734 B2
(45) Date of Patent: May 13, 2008

(54) OLIGONUCLEOTIDE COMPOSITIONS AND THEIR USE FOR THE MODULATION OF IMMUNE RESPONSES

(75) Inventors: Nigel C. Phillips, Point-Claire (CA); Mario C. Filion, Laval (CA)

(73) Assignee: Bioniche Life Sciences Inc., Belleville, Ontario (CA)

( * ) Notice: Subject to any disclaimer, the term of this patent is extended or adjusted under 35 U.S.C. 154(b) by 0 days.

(21) Appl. No.: 10/420,513

(22) Filed: Apr. 22, 2003

(65) Prior Publication Data

US 2004/0058883 A1 Mar. 25, 2004

Related U.S. Application Data

(60) Provisional application No. 60/374,540, filed on Apr. 22, 2002.

(51) Int. Cl.
| *A01N 37/18* | (2006.01) |
| *A01N 43/04* | (2006.01) |
| *A61K 38/00* | (2006.01) |
| *A61K 31/70* | (2006.01) |
| *A61K 45/00* | (2006.01) |
| *C07H 21/02* | (2006.01) |
| *C07H 21/04* | (2006.01) |

(52) U.S. Cl. ............................ 514/44; 514/12; 514/2; 536/23.1; 536/24.1; 536/24.33; 424/278.1

(58) Field of Classification Search ................. 514/44, 514/2, 12; 536/23.1, 23.6, 24.1, 24.33; 424/278.1
See application file for complete search history.

(56) References Cited

U.S. PATENT DOCUMENTS

| 6,239,116 B1 | 5/2001 | Krieg et al. | |
| 6,339,068 B1 * | 1/2002 | Krieg et al. | 514/44 |
| 6,809,081 B1 * | 10/2004 | Phillips et al. | 514/44 |
| 6,821,957 B2 * | 11/2004 | Krieg et al. | 514/44 |
| 7,087,586 B2 * | 8/2006 | Filion et al. | 514/44 |
| 7,157,436 B2 * | 1/2007 | Phillips et al. | 514/44 |
| 2003/0125290 A1 * | 7/2003 | Phillips et al. | 514/44 |
| 2003/0212026 A1 * | 11/2003 | Krieg et al. | 514/44 |
| 2004/0009949 A1 * | 1/2004 | Krieg | 514/44 |
| 2004/0067902 A9 * | 4/2004 | Bratzler et al. | 514/44 |
| 2004/0186067 A1 * | 9/2004 | Krieg et al. | 514/44 |
| 2004/0235774 A1 * | 11/2004 | Bratzler et al. | 514/44 |
| 2005/0032734 A1 * | 2/2005 | Krieg et al. | 514/44 |
| 2006/0154890 A1 * | 7/2006 | Bratzler et al. | 514/44 |
| 2006/0182793 A1 * | 8/2006 | Bachmann et al. | 424/450 |
| 2006/0211639 A1 * | 9/2006 | Bratzler et al. | 514/44 |
| 2006/0287263 A1 * | 12/2006 | Davis et al. | 514/44 |
| 2007/0066554 A1 * | 3/2007 | Krieg et al. | 514/44 |
| 2007/0184068 A1 * | 8/2007 | Renner et al. | 424/204.1 |

FOREIGN PATENT DOCUMENTS

| WO | WO 99/58118 A | 11/1999 |
| WO | WO 99/65924 A | 12/1999 |
| WO | WO 00/14217 A | 3/2000 |
| WO | WO 01/07055 A | 2/2001 |
| WO | WO 01/22990 A2 * | 4/2001 |
| WO | WO 01/44465 A | 6/2001 |
| WO | WO 01/68117 A | 9/2001 |
| WO | WO 03/024481 A | 3/2003 |
| WO | WO 03/028764 | * 4/2003 |

OTHER PUBLICATIONS

Wloch et al, Human Gene Therapy, 1998, 9:1439-1447.*
Lipford et al, Immunology, 2000, 101:46-52.*
Filion et al, Vaccine, 2004, 22:2480-2488.*
Harandi et al, J. Virology, 2003, 77/2:953-962.*
Klimuk et al, J. Invest. Dermatol., 2004, 122:1042-1049.*
Hartmann et al, Eur. J. Immunol., 2003, 33:1633-1641.*
Ballas et al, J. Immunology, 2001, 167:4878-4886.*
Jugde et al, Human Immunology, 2004, 65:218-230.*
Kwant et al, Vaccine, 2004, 22:3098-3104.*
Filion et al, Vaccine, 2003, 21:983-989.*
Dalpke et al, Immunology, 2002, 106:102-112.*
Filion et al, Expert Opinion Invest. Drugs, 2001, 10/12:2157-2165.*
Shen et al, Antisense and Nucleic Acid Drug Development, 2002, 12:155-164.*
Shen et al, FASEB Journal, 2001 15/5:A1199 abstract #946.12 FASEB Meeting of Mar. 2001.*
Shimosato et al, Animal Science Journal, 2004, 75:377-382.*
Levtin, New England J. Medicine, 1993, 329/19:1400-1405.*
Haynes, Science, 1993, 260:1279-1286.*
Bystryn, Cancer and Metastasis Reviews, 1990, 9:81-91.*
Kurtis et al, Trends inParasitology, 2001, 17/5:219-223.*
Arevalo-Herrera et al, Molecular Immunology, 2001, 38:443-455.*
Satoh et al, Fukushima Igaku Zasshi, 2002, 52/3:237-250.*
Dziadzio et al, Handbook of Experimental Pharmacology, 2004, 161(Pharmacology and Therapeutics of ASthma and COPD):273-285.*
McCluskie et al, Molecular Medicine, 1999, 5/5:287-300.*
Agrawal et al, Molecular Medicine Today, 2000, 6:72-81.*
Wohlleben et al, Trends in Immunology, Nov. 2001, 22/11:618-626.*
Krieg et al, Immunology Today, Oct. 2000, 21/10:521-526.*
Kline et al, Am. J. Physiol. Lung Cell Mol. Physiol., 2002, 283:L170-L179.*

(Continued)

*Primary Examiner*—Nita Minnifield
(74) *Attorney, Agent, or Firm*—Kilpatrick Stockton LLP

(57) ABSTRACT

The present invention relates to 3'-OH, 5'-OH polynucleotide sequence compositions and methods for activating an immune response in an individual, and more preferably, for activating antigen presenting cells in the individual. In one embodiment, the antigen presenting cell is a dendritic cell. The present invention also includes compositions and methods for activating dendritic cells in vitro. These dendritic cells may then be administered to an individual. Preferred 3'-OH, 5'-OH polynucleotide sequences comprise six bases wherein at least 50% of the bases are guanine and the 5' base is guanine. The compositions may comprise a phosphodiester or phosphorothioate backbone.

25 Claims, No Drawings

OTHER PUBLICATIONS

Kline et al, J. Immunology, 1998, 160:2555-2559.*
Donnelly, Nature Medicine, Nov. 2003m 9/11:1354-1356.*
de Gruijl et al, Nature Medicine, Oct. 1999, 5/10:1124-1125.*
Weiner, J. Leukoc. Biol., 2000, 68:455-463.*
Bitton, Current Opinion in Molecular Therapeutics, 2004, 6/1:17/26.*
Agrawal et al, Trends in Molecular Medicine, Mar. 2003, 8/3:114-121.*
Mempel et al, Immunology Letters, 2003, 89:47-57.*
Shen et al, J. Autoimmunity, 2005, 24:183-190.*
Holmgren et al, immunology Letters, 2005, 97:181-188.*
Krieg et al, Pharamcology and Therapeutics, 1999, 84:113-120.*
Senuma et al, Cytokine, Oct. 2002, 20/1:23-29.*
Staines, Medical Hypotheses, 2005, Article in Press, 5 pp.*
Garg et al, J. Autoimmunity, 1999, 11:371-378.*
Mocellin et al, Lancet Oncology, Dec. 2004, 5/12:727-737, abstract only.*
Hegmans et al, Am. J. Respir. Crti. Care Med., May 2005, 171/10:1168-1177 abstract only.*
Kao et al, Immunology Letters, Jun. 30, 2005, abstract only.*
Alexander et al, Cancer Immunol. Immunother., Jun. 18, 2005, abstract only.*
Foon et al, J. Clin. Oncol., Sep. 1999, 17/9:2889-2895 abstract only.*
Ridgway, Cancer Invest., 2003, 21/6:873-886.*
Ciurli et al, Clinical & Investigative Medicine, Aug. 2004, 27/4: Poster #29, Abstract only.*
Ciurli et al, Clinical & Investigative Medicine, Aug. 2004, 27/4: Poster #30 abstract only.*
Phillips et al, Cancer Detection and Prevention, 1990, 14/4:491-496.*
Phillips et al, Cancer Detection and Prevention, 1988, 12:451-459.*
Lang et al, Eur. J. Immunol. 1999, 29:3496-3506.*
Bates et al, JBC, 274/37:26369-26377.*
Goutteangeas et al, Nature Biotechnology, May 2000, 18:491-492.*
Bodey et al, Anticancer Research, 2000, 20:2665-2676.*
Trichopoulos et al, Scientific American, "What Causes Cancer?" Sep. 1996, 14 pages.*
Weinberg, Scientific American, "How Cancer Arises", Sep. 1996, 14 pages.*
Old, Scientific American, "Immunotherpay for Cancer", Sep. 1996, 12 pages.*
Saleh et al, Current Pharmaceutical Design, 2005, 11:3461-3473.*
Lee, et al., *J. of Immunology*, vol. 165, pp. 3631-3639, 2000.
Krieg, "CpG Motifs in Bacterial DNA and Their Immune Effects", *Annu. Rev. Immunol.*, 2002, 20:709-760.
Sparwasser et al., "Bacterial DNA and Immunostimulatory CpG Oligonucleotides Trigger Maturation and Activation of Murine Dendritic Cells", *Eur. J. Immunol*, 1998, 28:2045-2054.
Hartman et al., "CpG DNA: A Potent Signal for Growth, Activation, and Maturation of Human Dendritic Cells", *Proc. Natl. Acad. Sci. USA*, 1999, 96:9305-9310.
Askew et al., "CpG DNA Induces Maturation of Dendritic Cells with Distinct Effects on Nascent and Recycling MHC-II Antigen-Processing Mechanisms", *J. Immunol.*, 2000, 165(12) 6889-6895, Dec. 2000.
Kadowaski et al., "Distinct CpG DNA and Polyinosinic-Polycytidylic Acid Double-Stranded RNA, Respectively, Stimulate CD11c-Type 2 Dendritic Cell Precursors and CD11c+ Dendritic Cells to Produce Type 1 IFN[1]" *J. Immunol.*, 2001, 166 (4):2291-2295.

* cited by examiner

SEQUENCE LISTING

<160> NUMBER OF SEQ ID NOS: 9

<210> SEQ ID NO 1
<211> LENGTH: 6
<212> TYPE: DNA
<213> ORGANISM: Artificial Sequence
<220> FEATURE:
<223> OTHER INFORMATION: Synthetic

<400> SEQUENCE: 1 gtgtgt                                                                      6

<210> SEQ ID NO 2
<211> LENGTH: 6
<212> TYPE: DNA
<213> ORGANISM: Artificial Sequence
<220> FEATURE:
<223> OTHER INFORMATION: Synthetic

<400> SEQUENCE: 2 ggtggg                                                                      6

<210> SEQ ID NO 3
<211> LENGTH: 6
<212> TYPE: DNA
<213> ORGANISM: Artificial Sequence
<220> FEATURE:
<223> OTHER INFORMATION: Synthetic

<400> SEQUENCE: 3 gggtgg                                                                      6

<210> SEQ ID NO 4
<211> LENGTH: 6
<212> TYPE: DNA
<213> ORGANISM: Artificial Sequence
<220> FEATURE:
<223> OTHER INFORMATION: Synthetic

<400> SEQUENCE: 4 ggccgg                                                                      6

<210> SEQ ID NO 5
<211> LENGTH: 6
<212> TYPE: DNA
<213> ORGANISM: Artificial Sequence
<220> FEATURE:
<223> OTHER INFORMATION: Synthetic

<400> SEQUENCE: 5 gggggg                                                                      6

<210> SEQ ID NO 6
<211> LENGTH: 6
<212> TYPE: DNA
<213> ORGANISM: Artificial Sequence
<220> FEATURE:
<223> OTHER INFORMATION: Synthetic

<400> SEQUENCE: 6 gggagg                                                                      6

<210> SEQ ID NO 7
<211> LENGTH: 6

```
<212> TYPE: DNA
<213> ORGANISM: Artificial Sequence
<220> FEATURE:
<223> OTHER INFORMATION: Synthetic

<400> SEQUENCE: 7 gggcgg                                                                    6

<210> SEQ ID NO 8
<211> LENGTH: 6
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(3)
OTHER INFORMATION: "n" = G, C, A or T
<220> FEATURE:
<221> NAME/KEY: misc_feature
<222> LOCATION: (4)..(4)
<223> OTHER INFORMATION: "n" = G, C, A or T

<400> SEQUENCE: 8 ggnngg                                                                    6

<210> SEQ ID NO 9
<211> LENGTH: 6
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(4)
<223> OTHER INFORMATION: "n" = G, C, A or T

<400> SEQUENCE: 9 gggngg                                                                    6
```

OLIGONUCLEOTIDE COMPOSITIONS AND THEIR USE FOR THE MODULATION OF IMMUNE RESPONSES

CROSS-REFERENCE TO RELATED APPLICATIONS

This application claims the priority benefit of U.S. Provisional Application No. 60/374,540 filed Apr. 22, 2002 in the United States Patent and Trademark Office.

FIELD OF THE INVENTION

The present invention relates to compositions comprising 3'-OH, 5'-OH phosphorothioate and phosphodiester polynucleotides and their use to modulate immune responses.

BACKGROUND OF THE INVENTION

Dendritic cells (DC) are antigen-presenting cells (APC) involved in the initiation of primary immune responses. Their functions vary with maturation. Immature DC are very effective in processing native protein antigens but lack sufficient cell surface MHC class II and co-stimulatory molecules for antigen presentation. Mature DC are less able to capture new proteins for presentation but are more efficient in the stimulation of resting CD4 and CD8 T lymphocytes. Morphologically, mature DC increase in cell size and granularity. Mature DC have increased levels of cell surface molecules MHC II, CD40, CD83 and co-stimulatory molecules CD80 and CD86. Activation of mature DC results in the synthesis of high levels of IL-12 that enhance both innate and acquired immunity.

Synthetic oligonucleotides are polyanionic sequences. Synthetic oligonucleotides are reported that bind selectively to nucleic acids, to specific cellular proteins, to specific nuclear proteins or to specific cell surface receptors. Synthetic phosphorothioate oligonucleotides of 8 to 100 bases containing a least one unmethylated CpG dinucleotide have been shown to stimulate the immune system (U.S. Pat. No. 6,239,116). In particular, synthetic phosphorothioate oligonucleotides containing a CpG motif (5'purine-purine-Cytosine-Guanine-pyrimidine-pyrimidine3') have been found to stimulate the synthesis of cytokines such as IL-6, IL-12, IFN-gamma, TNF-alpha, and GM-CSF, the lytic activity of natural killer cells and the proliferation of B lymphocytes (Krieg, Annu. Rev. Immunol. 2002, 20:709-760). Synthetic phosphorothioate oligonucleotides including a CpG motif wherein the number of bases is greater than 14 have been reported to trigger maturation and activation of dendritic cells: increase in cell size and granularity; synthesis of IL-12; increase in endocytosis; and, up-regulation of cell surface molecules MHC II, CD40, CD80, CD83 and CD86 (Sparwasser et al. Eur. J. Immunol. 1998, 28:2045-205; Hartman et al. Proc. Natl. Acad. Sci. USA 1999, 96:9305-9310; Askew et al. J. Immunol. 2000, 165:6889-6895). Synthetic phosphodiester oligonucleotides including a CpG motif wherein the number of bases is 30 have been reported to stimulate the synthesis of IFN and to up-regulate the expression of CD80 and CD86 on DC precursors (Kadowaski et al. J. Immunol. 2001 166:2291-2295).

We have previously described a composition comprising a 2 to 20 base 3'-OH, 5'-OH synthetic oligonucleotide selected from the group consisting of $(G_xT_y)_n$, $(T_yG_x)_n$, $a(G_xT_y)_n$, $a(T_yG_x)_n$, $(G_xT_y)_nb$, $(T_yG_x)_nb$, $a(G_xT_y)_nb$, and $a(T_yG_x)_nb$, wherein x and y is an integer between 1 and 7, n is an integer between 1 and 12, a and b are one or more As, Cs, Gs or Ts, wherein the oligonucleotide is between 2 and 20 bases. These compositions induce a response selected from the group consisting of induction of cell cycle arrest, inhibition of proliferation, induction of caspase activation, induction of apoptosis and stimulation of cytokine synthesis by monocytes and peripheral blood mononuclear cells (see PCT Publication No. WO 01/44465).

What is needed are new oligonucleotide compositions and methods for using these compositions to modulate the function of immune cells, including dendritic cells.

SUMMARY OF THE INVENTION

The present invention fulfills this need by providing an oligonucleotide composition comprising a six base 3'-OH, 5'-OH polynucleotide. In one embodiment, the phosphate backbone of the polynucleotide is a phosphodiester backbone. In another embodiment, the phosphate backbone of the polynucleotide is a phosphorothioate backbone. Preferably, the 3'-OH, 5'-OH polynucleotides are synthetic and more preferably, the 3'-OH, 5'-OH polynucleotides are selected from the group consisting of 5'GTGTGT3' (SEQ ID NO:1), 5'GGTGGG3' (SEQ ID NO:2), 5'GGGTGG3' (SEQ ID NO:3), 5'GGGGGG3' (SEQ ID NO:7), 5'GGGAGG3' (SEQ ID NO: 6), 5'GGGGGG3' (SEQ ID NO: 5) and 5'GGCCGG3' (SEQ ID NO: 4). The 3'-OH, 5'-OH polynucleotides stimulate an immune response when administered to a human or animal. The immune response may be systemic or local. In one embodiment, the 3'-OH, 5'-OH polynucleotides stimulated an APC in the human or animal to which the polynucleotides are administered. The 3'-OH, 5'-OH polynucleotides may also be administered to an APC directly in vitro for stimulation of the APC. The stimulated APC may then be administered to a human or an animal for the activation of an immune response in the human or animal.

When administered to a DC, the 3'-OH, 5'-OH polynucleotides of the present invention stimulate the DC by inducing a response selected from the group consisting of an increase in the production of IL-1 beta, IL-12 or IFN-gamma, an increase in cell size and granularity, an increase in endocytosis, an increase in expression of CD80, CD83, CD86 or MHC II at the cell surface, and a decrease in expression of OX-2 at the cell surface.

The present invention further provides a method of administering a composition comprising a 3'-OH, 5'-OH polynucleotide and a pharmaceutically acceptable carrier to an animal or a human in an amount effective to induce stimulation of an immune response in the animal or human, and more preferably, the stimulation of one or more APC in the animal or human. A preferred APC is a DC. In another embodiment, an antigen is administered to the animal or human in addition to the 3'-OH, 5'-OH polynucleotide composition, resulting in an antigen-specific immune response in the animal or human. Preferred antigens are tumor antigens and hepatitis surface antigen. In some embodiments, stimulation of one or more APC results in a systemic immune response in the animal or human. In other embodiments, the immune response is local. The present invention also includes methods of administering a composition comprising a 3'-OH, 5'-OH polynucleotide and a immunomodulatory agent, or modality, to animal or a human in an amount effective to induce stimulation of an immune response in the animal or human.

The present invention also provides a method comprising in vitro administration of a composition comprising a 3'-OH, 5'-OH polynucleotide and a pharmaceutically acceptable carrier to APC, and more preferably, DC, containing antigens, including tumor antigens, wherein such administration results in the stimulation of the APC. The method may further include introduction of the stimulated APC into an animal or human for the stimulation of an immune response in the animal or human. The unexpected and surprising ability of short six base 3'-OH, 5'-OH polynucleotides to stimulate APC such as DC provides an important benefit for animals and humans.

The methods described herein may be used for treating diseases such as cancer, for treating allergies, for vaccinating animals or humans against various pathogens, for treating autoimmune diseases and for preventing transplantation rejection. In some embodiments, the present invention achieves treatment of autoimmune diseases and prevention of transplantation rejection by increasing IL-12 synthesis. The synthesis of IL-12 can inhibit autoimmune diseases, transplantation rejection and graft-versus-host disease (GVHD), and allergies (See for example, Bagenstose et al., J. Immunol. 1998; 160:1612 (Downregulation of autoantibody production in autoimmunity by IL-12); Vogel et al., Eur. J. Immunol., 1996;26:219 (Inhibition of B1 lymphocyte, a B lymphocyte subset implicated in the development of autoimmunity, by IL-12); Dey et al., Blood, 1998;91:3315 (Inhibition of graft-versus-host disease (GVHD) by IL-12); Smits et al., Int. Arch Allergy Immunol., 2001;126-102 (Modification of the pathogenic Th2 immune profile toward a Th1 profile by IL-12 in the treatment of allergies)). In other embodiments, the present invention achieves treatment of autoimmune diseases and prevention of transplantation rejection through vaccination (See for example, Zhang et al., J. Mol. Med. 1996;74:653 (Vaccination against autoreactive B or T lymphocytes responsible for autoreactive diseases); Vignes et al., Eur. J. Immunol., 2000;30:2460 (Vaccination against alloreactive T lymphocytes responsible for graft rejection); Liu et al., J. Exp. Med., 2002;196: 1013 (Induction of immune tolerance by delivery of dying cells to activated DC cells in situ)).

Accordingly, it is an object of the present invention to provide a composition and method effective to treat a disease in an animal, including a human.

Another object of the present invention is to provide a composition and method effective to vaccinate an animal or human.

Yet another object of the present invention is to provide a composition and method effective to treat cancer in an animal or human.

Still another object of the present invention is to provide a composition and method effective to stimulate an immune response in an animal or human.

A further object of the present invention is to provide a composition and method effective to induce maturation and/or activation of APC, and preferably, DC, in an animal or human.

Another object of the present invention is to provide a composition and method effective to induce in vitro stimulation of APC containing an antigen for administration of the stimulated APC to an animal or human.

Yet another object of the present invention is to provide a composition and method effective to increase the production of IL-1beta, IL-12 and/or IFN gamma by DC.

Still another object of the present invention is to provide a composition and method effective to increase cell size and/or granularity of DC.

A further object of the present invention is to provide a composition and method effective to increase endocytosis by DC.

Another object of the present invention is to provide a composition and method effective to increase the level of CD40, CD80, CD86 and/or MHC II at the cell surface of DC.

Another object of the present invention is to provide a composition and method effective to decrease the level of OX-2 at the cell surface of DC.

Yet another object of the present invention is to provide a composition and method that potentiates the effect of other therapeutic or immunomodulatory agents.

Still another object of the present invention is to provide a composition and method that potentiates the effect of one or more cytokines on APC, and preferably, DC.

A further object of the present invention is to provide a composition and method that potentiates the effect of GM-CSF on DC.

These and other objects, features and advantages of the present invention will become apparent after a review of the following detailed description of the disclosed embodiment and the appended claims.

DETAILED DESCRIPTION OF THE INVENTION

The present invention provides a composition comprising an isolated 3'-OH, 5'-OH polynucleotide sequence comprising six bases, wherein at least 50% of the bases are guanine, the 5' base is guanine, wherein the composition stimulates an immune response in an animal or a human to which the composition is administered. The present invention also provides a method including administration of a composition comprising a 3'-OH, 5'-OH polynucleotide and a pharmaceutically acceptable carrier to an animal or a human in an amount effective to stimulate one or more antigen-presenting cells (APC), or preferably one or more DC, in the animal or human. The stimulation of one or more APC in the animal or human may result in a systemic immune response or a local immune response. The present invention also provides a method including in vitro administration of a composition comprising a 3'-OH, 5'-OH polynucleotide to an APC containing an antigen in an amount effective to stimulate the APC. These APC may then be administered to an animal or human with a pharmaceutically acceptable carrier for stimulation of an immune response. The unexpected and surprising ability of six base, 3'-OH, 5'-OH synthetic phosphodiester and phosphorothioate oligonucleotides to induce stimulation of APC such as DC provides an important benefit for animals and humans.

As used herein the term "3'-OH, 5'-OH polynucleotide" refers to a polynucleotide having hydroxyl moieties at both its 3' and 5' ends. More particularly, the 3'-OH, 5'-OH polynucleotides of the present invention comprise a hydroxyl moiety at the 3' carbon of the sugar at the 3' end of the polynucleotide and comprise a hydroxyl moiety at the 5' carbon of the sugar at the 5' end of the polynucleotide. In one embodiment of the present invention, the 3'-OH, 5'-OH polynucleotide consists of six nucleotide bases. Preferably, the 3'-OH, 5'-OH polynucleotide comprises six nucleotide bases wherein at least 50% of those nucleotide bases are guanine (G) and wherein the S nucleotide base is G. In a more preferred embodiment, the 3'-OH, 5'-OH polynucleotide comprises or consists of a 5'GGNNGG3'(SEQ ID NO: 8) sequence or a 5'GGGNGG3' (SEQ ID NO:9) sequence wherein N is G, C, A or T. The 3'-OH, 5'-OH polynucleotide may specifically comprise or consist of a sequence selected from the group consisting of 5'GTGTGT3'(SEQ ID NO:1), 5'GGTGGG3' (SEQ ID NO:2), 5'GGGTGG3'(SEQ ID NO:3), 5 'GGCCGG3'(SEQ ID NO:4), 5'GGGGGG3' (SEQ ID NO:5), 5'GGGAGG3' (SEQ ID NO:6) and 5'GGGCGG3' (SEQ ID NO:7). In one embodiment, the 3'-OH, 5'-OH polynucleotides are administered to an APC, a DC, a human, or an animal in a vector.

These 3'-OH, 5'-OH polynucleotides may contain a phosphodiester backbone or a modified phosphate backbone such as a phosphorothioate backbone. The 3'-OH, 5'-OH polynucleotides containing a phosphodiester backbone that correspond to the above-described sequence numbers are designated hereinafter as follows: 5'GTGTGT3' (SEQ ID NO:1) (N1A), 5'GGTGGG3' (SEQ ID NO:2) (N2A), 5'GGGTGG3' (SEQ ID NO:3) (N3A), 5'GGCCGG3' (SEQ ID NO:4) (N4A), 5'GGGGGG3' (SEQ ID NO:5) (N5A), 5'GGGAGG3' (SEQ ID NO:6) (N6A) and 5'GGGCGG3' (SEQ ID NO:7) (N7A). In these embodiments, each nucleotide in the polynucleotide chain is a phosphodiester nucleotide. The 3'-OH, 5'-OH polynucleotides containing a phosphorothioate backbone that correspond to the above-described sequence numbers are designated hereinafter as follows: 5' GTGTGT3' (SEQ ID NO:1) (NIB), 5'GGTGGG3' (SEQ ID NO:2) (N2B), 5'GGGTGG3' (SEQ ID NO:3) (N3B), 5'GGCCGG3' (SEQ ID NO:4) (N4B), 5'GGGGGG3' (SEQ ID NO:5) (NSB), 5'GGGAGG3' (SEQ ID NO:6) (N6B) and 5'GGGCGG3' (SEQ ID NO:7) (N7B). In these embodiments, each nucleotide in the polynucleotide chain is a phosphorothioate nucleotide. The present invention also encompasses 3'-OH, 5'-OH polynucleotides that include one or more phosphodiester nucleotides and one or more phosphorothioate nucleotides. Preferably, the 3 '-OH, 5'-OH polynucleotides are N1A, N2B, N3B or N5B, and more preferably, N3B or N5B.

As also used herein, the terms "stimulate" and "stimulates" refer to the activation or maturation of a DC, or another APC, or to the activation or increase of an immune response, depending upon the context of the terms' use. Stimulation of a DC may be evidenced by an increase in the cell size and/or granularity; an increase in the production of IL-1beta, IL-12 and/or IFN-gamma; an increase in endocytosis; an increase in the cell-surface expression of CD80, CD83, CD86, MHC II, or any combination thereof; a decrease in the cell-surface expression of OX-2; or any combination thereof. Accordingly, a "dendritic cell response" includes, but is not limited to, an increase in the cell size and/or granularity; an increase in the production of IL-1 beta, IL-12 or IFN-gamma; an increase in endocytosis; an increase in the cell-surface expression of CD80, CD83, CD86, or MHC 11; a decrease in the cell-surface expression of OX-2; or any combination thereof. The terms "dendritic cell" and "DC" include, but are not limited to, interstitial DC, Langheran's cell-derived DC, plasmacytoid DC and any progenitors of the aforementioned cells. As used herein, the term "production" refers to the synthesis and/or secretion of a molecule. In a preferred embodiment, the dendritic cell is an interstitial DC.

It is believed that the 3'-OH, 5'-OH polynucleotides described herein are not only able to stimulate DC, but are also able to stimulate other APC including professional APC such as, but not limited to, monocytes, macrophages, Langerhans' cells, B lymphocytes, T lymphocytes, Kupffer cells, microglia, Schwann cells and endothelial cells; and non-professional APC such as, but not limited to, epithelial cells, fibroblasts, melanocytes, neural cells, smooth muscle cells, myocytes, hepatocytes, astrocytes and keratinocytes. Accordingly, the present invention includes compositions and methods for the activation of an APC.

When referring to an immune response, the term "stimulate" refers to an activation of the immune system generally or to an activation of components of the immune system in an antigen non-specific manner unless otherwise indicated. Stimulation of an immune response in an individual may be evidenced by, but is not limited to, cellular proliferation, clonal expansion, synthesis of new proteins, differentiation into effector cells, differentiation into memory cells, an increase in the level or amount of a type of antibody, a switch in the antibody class, somatic hypermutation in antibody-producing B lymphocytes, an increase in the level or amount of a type of immune cell, recruitment (motility and migration) of immune cells in a particular location, an increase in the level or amount of a cytokine in an individual, an increase in the level or amount of a chemokine in an individual, increased antigen presentation, increased endocytosis, an increase or acquisition of co-stimulatory molecules (accessory molecules), an increase or acquisition of adhesion molecules, an increase or acquisition of cytokine receptors, an increase or acquisition of chemokine receptors, increased cell-mediated cytotoxicity, morphological changes, establishment of immune cell memory, an increase in the level or amount of reactive oxygen intermediates, an increase in the level or amount of nitric oxide, an increase in the level or amount of neuroendocrine molecules (e.g., hormones, neurotransmitters, etc.) and a break of immune tolerance or suppression. Immune cells include, but are not limited to, lymphocytes such as B cells, T cells, including $CD4^+$ and $CD8^+$ cells, and NK cells; mononuclear phagocytes; granulocytes such as neutrophils, eosinophils and basophils; dendritic cells as described herein; and any progenitors of the aforementioned cells. Antibody types include IgG, IgA, IgM, IgD, IgE and IgY.

In one embodiment, the immune response is a systemic immune response. The term "systemic immune response" refers herein to an immune response that is not restricted to a particular area of the body. An example of a systemic immune response is an increase in the level of an antibody circulating in the circulatory or lymphatic system in an individual following administration of an antigen and an immunostimulatory molecule to the individual. Another example is an increase in the level of a cytokine and/or a chemokine in the circulatory or lymphatic system in an individual following administration of an immunostimulatory molecule to the individual. Another example is the presence of sensitized immune effector cells such as T-cells, B-cells or plasma cells capable of responding to challenge with sensitizing antigen in the blood or lymphatic circulation or in immune system organs such as the spleen, lymph nodes or liver. In other embodiments, the immune response is a local immune response. The term "local immune response" refers an immune response that is primarily, but not necessarily wholly, restricted to a particular area of the body. A local immune response may be evidenced by localized swelling or redness and/or recruitment (motility and migration) of immune cells to a particular area of the body. For example, a mucosal immune response may occur following mucosal administration of an antigen and/or an immunostimulatory molecule such as a 3'-OH, 5'-OH polynucleotide described herein. A mucosal response may include, but are not limited to, an increase in the level or amount of a type of antibody, an increase in the level or amount of IgA antibody, activation of gamma/delta-positive T lymphocytes, induction of local immune tolerance and induction of systemic immune tolerance.

In several embodiments of the present invention, the 3'-OH, 5'-OH polynucleotides are administered to an individual (i.e., an animal or a human) for the treatment or prevention of a disease. As used herein, the term "disease" refers to a condition wherein bodily health is impaired and includes, but is not limited to, a cancer; an infection by a pathogen including a virus, bacteria or parasite; an allergy; an autoimmune disease; and an autoimmune response to a transplanted organ. In some embodiments, the disease is associated with DC malfunction including, but not limited to, Sezary syndrome (patients have a profound defect in circulating DC) (Wysocka et al., Blood 2002, 100:3287); Down's syndrome (patients have a dendritic atrophy) (Takashima et al., J. Intellect. Disabil. Res. 1994, 38:265); autoimmune diseases involving inappropriate activation of DC (e.g., prolonged presentation of self antigen by DC) (Erikson et al., J. Exp. Med. 2003, 197:323 and Ludewig et al., Curr. Opin. Immunol. 2001, 13:657); spinal cord injury (patients have a dendritic atrophy) (Iversen et al., Blood 2000, 96:2081); and Graves' disease (thyroidal dendritic cells are implicated in the disease) (Quadbeck et al., Scand. J. Immunol. 2002, 55:612). The term "treatment" refers to the lessening of a disease symptom and does not require curing of the disease. As also used herein, the term "effective amount" refers to an amount of a 3'-OH, 5'-OH polynucleotide effective to induce an immune response. The therapeutic effectiveness of a 3'-OH, 5'-OH polynucleotide may be increased by methods including, but not limited to, chemically modifying the base, sugar or phosphate backbone, chemically supplementing or biotechnologically amplifying the sequences using bacterial plasmids containing the appropriate sequences, complexing the sequences to biological or chemical carriers or coupling the sequences to cell-type directed ligands or antibodies.

The 3'-OH, 5'-OH polynucleotides of the present invention may be combined with pharmaceutically acceptable carriers and administered to a cell as compositions, preferably an APC, and more preferably a DC, in vitro or in vivo. In one embodiment of the present invention, a composition comprising a 3'-OH, 5'-OH polynucleotide is administered to a DC in vitro in an amount effective to stimulate the DC. The DC is then administered to an animal or human with a pharmaceutically acceptable carrier for stimulation of an immune response in the animal or human. In a preferred embodiment, the dendritic cell is an immature DC having a characteristic including, but not limited to, the following: high intracellular level of MHC II; high endocytic activity; high levels of specific chemokine receptors CCR1, CCR2, CCR3, CCR5, CCR6 and CXRC1; a low level of CCR7; high levels of CD36, CD68, CD47 and CD91 molecules; low levels of co-stimulatory CD40, CD54, CD58, CD80 and CD83 molecules; absence of DC-LAMP (LAMP; lysosome-associated membrane protein); presence of DCIR (DC immunoreceptor), CLEC-1 (C-lectin receptor), DC-ASGPR (DC-asialoglycoprotein), MN (mannose receptor), TLR-2 and -3 (Toll-like receptor), FCγ R, FCεR, integrin $\alpha v \beta 5$ and $\alpha_v \beta 3$ at the cell surface. Immature DC may be found in peripheral blood. In a further preferred embodiment, the immature DC contains, or is exposed to, an antigen prior to the administration of the 3'-OH, 5'-OH polynucleotide to the DC. Non-limiting methods of obtaining DC containing antigen include antigen pulsing and the use of genetically modified DC expressing one or several antigens It is to be understood that one or more 3'-OH, 5'-OH polynucleotides may be administered to a DC in vitro either alone or in combination with other immunomodulatory agents that affect DC containing antigens, including tumor antigens, in a amount effective to induce stimulation of DC designed to be re-injected to an animal or human, for the stimulation of the immune response. Immunomodulatory agents include, but are not limited to the following: aluminum hydroxide; aluminum phosphate; calcium phosphate; polymers; co-polymers such as polyoxyethylene-polyoxypropylene copolymers, including block co-polymers; polymer P1005; Freund's complete adjuvant (for animals); Freund's incomplete adjuvant; sorbitan monooleate; squalene; CRL-8300 adjuvant; QS 21; saponins; ISCOM; muramyl dipeptide; glucosaminylmuramyl dipeptide; trehalose; bacterial extracts, including mycobacterial extracts; bacterial whole cells, including mycobacterial whole cells; detoxified endotoxins; membrane lipids; DNA isolated from prokaryotic organisms, CpG synthetic oligonucleotides; non-CpG synthetic oligonucleotides; apatamers; plasmids immunostimulatory molecules; poly (I:C) molecules; cytokines; chemokines; chitosan and derivatives; hyaluronic acid and derivatives; cholera toxin; pertussis toxin; and, keyhole limpet hemocyanin, or combinations thereof. The 3 '-OH, 5'-OH polynucleotide or 3'-OH, 5 '-OH polynucleotide plus immunomodulatory agent can be added to DC in a single treatment or in multiple treatments, optionally at different concentrations, and over a period of time appropriate for the stimulation of DC. The 3'-OH, 5'-OH polynucleotide can be added before, at the same time, or after administration of the immunomodulatory agents. Moreover, the 3'-OH, 5'-OH polynucleotide can be added before, at the same time, or after administration of the antigen(s).

The present invention also includes methods of administering a 3'-OH, 5'-OH polynucleotide and an antigen not contained within a DC to an animal or human, wherein such administration results in an immune response in the animal or human, and more preferably, an antigen-specific immune response. The antigen may be administered to the animal or human prior to, at the same time or following the administration of the 3'-OH, 5'-OH polynucleotide. In a preferred embodiment, the antigen is administered at the same time as the 3'-OH, 5'-OH polynucleotide.

The antigens described herein are not limited to any particular antigen or type of antigen. In one embodiment, the antigen is a tumor antigen, such as a tumor antigen derived from a tumor cell lysate. In another embodiment, the antigen is an antigen derived from a pathogen, and more preferably an antigen expressed on the surface of the pathogen. One example of a pathogen derived surface antigen is the hepatitis surface antigen. When the antigen is administered to the animal or human not contained within a DC, the antigen may be administered as a protein, peptide or polypeptide, or a polynucleotide encoding the antigen may be administered. The polynucleotide encoding the antigen may be contained within a vector comprising other elements that will allow for expression of the antigen polypeptide in the animal or human. In one embodiment, the antigen and the 3'-OH, 5'-OH polynucleotide are contained within different vectors.

Administration of a 3'-OH, 5'-OH polynucleotide stimulated DC containing an antigen, or administration of a 3'-OH, 5'-OH polynucleotide and antigen to an animal or human results in stimulation of an immune response in the animal or human. In preferred embodiments, such administrations result in stimulation of the immune system in conjunction with an antigen-specific immune response in the animal or human. The term "antigen-specific immune response" refers to an immune response that is predominantly directed toward the antigen. An antigen-specific immune response includes or consists of an increase in the amount of an antibody (antibody titer), a switch in the antibody class, somatic hypermutation in antibody-producing B lymphocytes, establishment of immune cell memory, increase in the amount of cells bearing a specific B cell receptor or T cell receptor for the antigen in the human or animal to which the antigen is administered. An antibody is "specific for" a particular antigen when the antibody binds to the antigen with sufficient affinity and avidity to result in the production of an antibody-antigen complex.

Forms of administration include, but are not limited to, injections, solutions, creams, gels, implants, pumps, ointments, emulsions, suspensions, microspheres, particles, microparticles, nanoparticles, liposomes, pastes, patches, tablets, transdermal delivery devices, sprays, aerosols, or other means familiar to one of ordinary skill in the art. Pharmaceutical formulations of the present invention can be prepared by procedures known in the art using well-known and readily available ingredients. For example, the compounds can be formulated with common excipients, diluents, or carriers, and formed into tablets, capsules, suspensions, powders, and the like. Examples of excipients, diluents, and carriers that are suitable for such formulations include the following: fillers and extenders (e.g., starch, sugars, mannitol, and silicic derivatives); binding agents (e.g., carboxymethyl cellulose and other cellulose derivatives, alginates, gelatin, and polyvinyl-pyrrolidone); moisturizing agents (e.g., glycerol); disintegrating agents (e.g., calcium carbonate and sodium bicarbonate); agents for retarding dissolution (e.g., paraffin); resorption accelerators (e.g., quaternary ammonium compounds); surface active agents (e.g., cetyl alcohol, glycerol monostearate); adsorptive carriers (e.g., kaolin and bentonite); emulsifiers; preservatives; sweeteners; stabilizers; coloring agents; perfuming agents; flavoring agents; lubricants (e.g., talc, calcium and magnesium stearate); solid polyethyl glycols; and mixtures thereof.

The formulations can be so constituted that they release the active ingredient only or preferably in a particular location, possibly over a period of time (i.e., a sustained-release formulation). Such combinations provide yet a further mechanism for controlling release kinetics. The coatings, envelopes, and protective matrices may be made, for example, from polymeric substances or waxes.

Compositions comprising one or more 3'-OH, 5'-OH polynucleotides and a pharmaceutically acceptable carrier are prepared by uniformly and intimately bringing into association the 3'-OH, 5'-OH polynucleotide and the pharmaceutically acceptable carrier. Pharmaceutically acceptable carriers include liquid carriers, solid carriers or both. Liquid carriers are aqueous carriers, non-aqueous carriers or both, and include, but are not limited to, aqueous suspensions, oil emulsions, water-in-oil emulsions, water-in-oil-in-water emulsions, site-specific emulsions, long-residence emulsions, sticky-emulsions, microemulsions and nanoemulsions. Solid carriers are biological carriers, chemical carriers or both and include, but are not limited to, viral vector systems, particles, microparticles, nanoparticles, microspheres, nanospheres, minipumps, bacterial cell wall extracts and biodegradable or non-biodegradable natural or synthetic polymers that allow for sustained release of the oligonucleotide compositions. Emulsions, minipumps and polymers can be implanted in the vicinity of where delivery is required (Brem et al., J. Neurosurg. 74: 441, 1991). Methods used to complex 3'-OH, 5'-OH polynucleotides to a solid carrier include, but are not limited to, direct adsorption to the surface of the solid carrier, covalent coupling to the surface of the solid carrier, either directly or via a linking moiety, and covalent coupling to the polymer used to make the solid carrier. Optionally, a sequence(s) can be stabilized by the addition of non-ionic or ionic polymers such as polyoxyethylenesorbitan monooleates (TWEENs) or hyaluronic acid.

Preferred aqueous carriers include, but are not limited to, water, saline and pharmaceutically acceptable buffers. Preferred non-aqueous carriers include, but are not limited to, a mineral oil or a neutral oil including, but not limited to, a diglyceride, a triglyceride, a phospholipid, a lipid, an oil and mixtures thereof, wherein the oil contains an appropriate mix of polyunsaturated and saturated fatty acids. Examples include, but are not limited to, soybean oil, canola oil, palm oil, olive oil and myglyol, wherein the fatty acids can be saturated or unsaturated. Optionally, excipients may be included regardless of the pharmaceutically acceptable carrier used to present the 3, -OH, 5'-OH polynucleotide compositions to cells. These excipients include, but are not limited to, anti-oxidants, buffers, and bacteriostats, and may include suspending agents and thickening agents.

One or more 3'-OH, 5'-OH polynucleotides may be administered to a human or an animal alone, or in combination with other immunomodulatory modalities including, but not limited to, the following: aluminum hydroxide; aluminum phosphate; calcium phosphate; polymers; co-polymers such as polyoxyethylene-polyoxypropylene copolymers, including block co-polymers; polymer P1005; Freund's complete adjuvant (for animals); Freund's incomplete adjuvant; sorbitan monooleate; squalene; CRL-8300 adjuvant; QS 21; saponins; ISCOM; muramyl dipeptide; glucosaminylmuramyl dipeptide; trehalose; bacterial extracts, including mycobacterial extracts; bacterial whole cells, including mycobacterial whole cells; detoxified endotoxins; membrane lipids; DNA isolated from prokaryotic organisms, CpG synthetic oligonucleotides; non-CpG synthetic oligonucleotides; apatamers; plasmids encoding immunostimulatory molecules; poly (I:C) molecules; cytokines; chemokines; chitosan and derivatives; hyaluronic acid and derivatives; cholera toxin; pertussis toxin and keyhole limpet hemocyanin or combinations thereof.

Also, one or more 3'-OH, 5'-OH polynucleotides may be administered alone, or in combination with other therapeutic modalities including, but not limited to, chemotherapeutic agents, antimicrobial agents, or antiviral agents. Chemotherapeutic agents include, but are not limited to, anti-metabolites, DNA damaging, microtubule destabilizing, microtubule stabilizing, actin depolymerizing, growth inhibiting, topoisomerase inhibiting, HMG-CoA inhibiting, purine inhibiting, pyrimidine inhibiting, metalloproteinase inhibiting, CDK inhibiting, angiogenesis inhibiting and differentiation enhancing. Dosages and methods of administration of these other therapeutic modalities are known to one of ordinary skill in the art.

Methods of administering the 3'-OH, 5'-OH polynucleotides of the present invention, APC or DC cells containing the 3 'OH, 5'-OH polynucleotides, or compositions comprising 3'-OH, 5'-OH polynucleotides and other materials such as carriers of the present invention that are particularly suitable for various forms include, but are not limited to the following types of administration, oral (e.g., buccal or sublingual), anal, rectal, as a suppository, topical, parenteral, nasal, aerosol, inhalation, intrathecal, intraperitoneal, intravenous, intraarterial, transdermal, intradermal, subdermal, subcutaneous, intramuscular, intratissular (e.g., tissue or gland), intrauterine, vaginal, into a body cavity, surgical administration at the location of a tumor or internal injury, directly into tumors, into the lumen or parenchyma of an organ, into bone marrow and into any mucosal surface of the gastrointestinal, reproductive, urinary and genitourinary system. In a preferred embodiment, the 3'-OH, 5'-OH polynucleotides of the present invention are administered to a mucosal surface selected from the group consisting of intravesical (inner bladder), ocular, oral, nasal, rectal and vaginal surface. Techniques useful in the various forms of administrations mentioned above include but are not limited to, topical application, ingestion, surgical administration, injections, sprays, transdermal delivery devices, osmotic pumps, electrodepositing directly on a desired site, or other means familiar to one of ordinary skill in the art. Sites of application can be external, such as on the epidermis, or internal, for example a gastric ulcer, a surgical field, or elsewhere.

The compositions of the present invention can be applied in the form of creams, gels, solutions, suspensions, liposomes, particles, or other means known to one of skill in the art of formulation and delivery of the compositions. Ultrafine particle sizes can be used for inhalation delivery of therapeutics. Some examples of appropriate formulations for subcutaneous administration include, but are not limited to, implants, depot, needles, capsules, and osmotic pumps. Some examples of appropriate formulations for vaginal administration include but are not limited to creams and rings. Some examples of appropriate formulations for oral administration include but are not limited to: pills, liquids, syrups, and suspensions. Some examples of appropriate formulations for transdermal administration include but are not limited to gels, creams, pastes, patches, sprays, and gels. Some examples of appropriate delivery mechanisms for subcutaneous administration include, but are not limited to, implants, depots, needles, capsules, and osmotic pumps. Formulations suitable for parenteral administration include, but are not limited to, aqueous and non-aqueous sterile injection solutions which may contain anti-oxidants, buffers, bacteriostats and solutes which render the formulation isotonic with the blood of the intended recipient, and aqueous and non-aqueous sterile suspensions which may include suspending agents and thickening agents. Extemporaneous injection solutions and suspensions may be prepared from sterile powders, granules and tablets commonly used by one of ordinary skill in the art.

Embodiments in which the compositions of the invention are combined with, for example, one or more pharmaceutically acceptable carriers or excipients may conveniently be presented in unit dosage form and may be prepared by conventional pharmaceutical techniques. Such techniques include the step of bringing into association the compositions containing the active ingredient and the pharmaceutical carrier(s) or excipient(s). In general, the formulations are prepared by uniformly and intimately bringing into association the active ingredient with liquid carriers. Preferred unit dosage formulations are those containing a dose or unit, or an appropriate fraction thereof, of the administered ingredient. It should be understood that in addition to the ingredients particularly mentioned above, formulations comprising the compositions of the present invention may include other agents commonly used by one of ordinary skill in the art.

The volume of administration will vary depending on the route of administration. Such volumes are known to one of ordinary skill in the art of administering compositions to animals or humans. Depending on the route of administration, the volume per dose is preferably about 0.001 to 100 ml per dose, more preferably about 0.01 to 50 ml per dose and most preferably about 0.1 to 30 ml per dose. For example, intramuscular injections may range in volume from about 0.1 ml to 1.0 ml. The oligonucleotide compositions administered alone, or together with other therapeutic agent(s), can be administered in a single dose treatment, in multiple dose treatments, or continuously infused on a schedule and over a period of time appropriate to the disease being treated, the condition of the recipient and the route of administration. Moreover, the other therapeutic agent can be administered before, at the same time as, or after administration of the oligonucleotide compositions.

Preferably, the amount of 3'-OH, 5'-OH polynucleotide administered per dose is from about 0.0001 to 100 mg/kg body weight, more preferably from about 0.001 to 10 mg/kg body weight and most preferably from about 0.01 to 5 mg/kg body weight. The particular 3'OH, 5'-OH polynucleotide and the particular therapeutic agent administered, the amount per dose, the dose schedule and the route of administration should be decided by the practitioner using methods known to those skilled in the art and will depend on the type of disease, the severity of the disease, the location of the disease and other clinical factors such as the size, weight and physical condition of the recipient. In addition, in vitro assays may optionally be employed to help identify optimal ranges for sequence and for sequence plus therapeutic agent administration.

The following examples will serve to further illustrate the present invention without, at the same time, however, constituting any limitation thereof. On the contrary, it is to be clearly understood that resort may be had to various other embodiments, modifications, and equivalents thereof which, after reading the description herein, may suggest themselves to those skilled in the art without departing from the spirit and scope of the invention.

EXAMPLE 1

Preparation of 3'-OH, 5'-OH-polynucleotides

The 3'-OH, 5'-OH polynucleotide sequences were prepared by Sigma-Genosys (Woodlands, Tex.) using Abacus Segmented Synthesis Technology. Unless stated otherwise, the sequences were dispersed in autoclaved deionized water or in a pharmaceutically acceptable buffer such as, but not limited to, saline immediately prior to use. The following sequences were used; N1A, N1B, N2A, N2B, N3A, N3B, N4A, N4B, N5A, N5B, N6A, N6B, N7A and N7B.

EXAMPLE 2

Dendritic Cells

Human dendritic cells were obtained from Clonetics (San Diego, Calif., USA) and were cultured in the medium recommended by Clonetics. DC were obtained from three different individuals (see Table 1). Major histocompatability typing was performed on each of these individuals and several of the HLA (human leukocyte antigens) types are shown.

TABLE 1

| DC characteristics | | | | | | |
|---|---|---|---|---|---|---|
| Individual | Sex | Age | HLA-A | HLA-B | HLA-C | HLA-DRB1 |
| A | F | 32 | 0201 30 | 41 62 | 03 17 | 04 08 |
| B | M | 22 | 0201 23 | 37 51 | 06 15 | 04 13 |
| C | F | 31 | 0201 11 | 08 35 | 04 07 | 03 13 |

EXAMPLE 3

Increase in Cell Size and Granularity of DC Cultured with 3'-OH, 5'-OH Polynucleotides DC were seeded in 1.0 ml at $1.0 \times 10^5$ cells/ml in 6-well flat-bottomed tissue culture plates for 48 hours with 100 μg of 6 base N1A, N1B, N2A, N2B, N3A, N3B, N4A, N4B, N5A, N5B, N6A, N6B, N7A or N7B polynucleotides. Cell size (FCS: forward side scatter) and granularity (S SC: side light scatter) were determined by flow cytometry using a FACSCalibur and analyzed using the CELLQuest Pro software (both from Becton-Dickinson, San Diego, Calif., USA). Percentage of DC showing a FCS>500 units and a SSC>400 units have been determined after treatment with 3-OH, 5-OH polynucleotides for DC isolated from three different individuals.

TABLE 2

Percentage of DC showing a FCS > 500 units and a SSC > 400 units after treatment with 3-OH, 5-OH polynucleotides. The percentage is based upon the total population of each group of DC as determined by FACS.

| | DC isolated from individual | | |
|---|---|---|---|
| SEQUENCE | A | B | C |
| unstimulated | 7 | 10 | 20 |
| N1A | 6 | 9 | 18 |
| N1B | 5 | 17 | 25 |
| N2A | 6 | 14 | 21 |
| N2B | 42 | 38 | 50 |
| N3A | 8 | 15 | 31 |
| N3B | 28 | 25 | 28 |
| N4A | 4 | n.d. | 19 |
| N4B | 4 | n.d. | 32 |
| N5A | 10 | 19 | 36 |
| N5B | 53 | 16 | 23 |
| N6A | 9 | 22 | 21 |
| N6B | 4 | 17 | 36 |
| N7A | 8 | n.d. | 30 |
| N7B | 16 | n.d. | 31 |

As shown in Table 2, a number of sequences induced the stimulation/maturation of DC as determined by their increase in cell size (FCS) and granularity (SSC).

EXAMPLE 4

Induction of IL-1 Beta Production

DC were seeded in 1.0 ml at $1.0 \times 10^5$ cells/ml in 6-well flat-bottomed tissue culture plates for 48 hours with 100 μg of 6 base N1A, N1B, N2A, N2B, N3A, N3B, N4A, N4B, N5A, N5B, N6A, N6B, N7A or N7B polynucleotides. Production of IL-1beta was determined in 100 μl of culture supernatant using a commercial ELISA (BioSource, Camarillo, Calif., USA) after 48 hours of incubation. Results are expressed as the "fold" (x) increase in IL-1beta production by treated DC compared to control cells.

TABLE 3

IL-1beta production by DC (fold increase compared to untreated DC)

| | DC isolated from individual | | |
|---|---|---|---|
| SEQUENCE | A | B | C |
| N1A | 1.0 | 1.2 | 1.0 |
| N1B | 1.0 | 1.0 | 1.0 |

TABLE 3-continued

IL-1beta production by DC (fold increase compared to untreated DC)

| | DC isolated from individual | | |
|---|---|---|---|
| SEQUENCE | A | B | C |
| N2A | 1.0 | 1.0 | 1.0 |
| N2B | 1.2 | 1.4 | 1.0 |
| N3A | 1.1 | 1.1 | 1.0 |
| N3B | 1.7 | 4.4 | 2.1 |
| N4A | 0.9 | n.d. | 1.0 |
| N4B | 1.0 | n.d. | 1.0 |
| N5A | 1.1 | 1.1 | 1.0 |
| N5B | 5.0 | 7.5 | 3.7 |
| N6A | 1.0 | 1.1 | 0.9 |
| N6B | 1.0 | 1.1 | 1.0 |
| N7A | 1.1 | n.d. | 1.0 |
| N7B | 1.1 | n.d. | 0.9 |

As shown in Table 3, polynucleotide N3B and polynucleotide N5B induced the production of IL-1beta in cells from the three individuals tested.

EXAMPLE 5

Induction of IL-12 Production

DC were seeded in 1.0 ml at $1.0 \times 10^5$ cells/ml in 6-well flat-bottomed tissue culture plates for 48 hours with 100 μg of 6 base N1A, N1B, N2A, N2B, N3A, N3B, N4A, N4B, N5A, N5B, N6A, N6B, N7A or N7B polynucleotides. Production of IL-12 was determined in 100 μl of culture supernatant using a commercial ELISA (BioSource) after 48 hours of incubation. Results are expressed as the "fold" (x) increase in IL-12 production by treated DC compared to control cells.

TABLE 4

IL-12 production by DC (fold increase compared to untreated DC)

| | DC isolated from individual | | |
|---|---|---|---|
| SEQUENCE | A | B | C |
| N1A | 15.9 | 17.8 | 2.1 |
| N1B | 1.5 | 1.3 | 1.1 |
| N2A | 7.9 | 6.8 | 1.6 |
| N2B | 1.3 | 6.0 | 2.5 |
| N3A | 1.0 | 1.0 | 1.0 |
| N3B | 5.2 | 17.3 | 14.4 |
| N4A | 1.2 | n.d. | 1.0 |
| N4B | 1.3 | n.d. | 2.6 |
| N5A | 0.9 | 1.1 | 1.0 |
| N5B | 7.5 | 17.8 | 15.0 |
| N6A | 1.0 | 1.0 | 1.0 |
| N6B | 1.3 | 1.4 | 4.1 |
| N7A | 1.0 | n.d. | 0.9 |
| N7B | 1.8 | n.d. | 1.0 |

As shown in Table 4, a number of sequences induced the production of IL-12.

EXAMPLE 6

Induction of IFN-Gamma Production

DC were seeded in 1.0 ml at $1.0 \times 10^5$ cells/ml in 6-well flat-bottomed tissue culture plates for 48 hours with 100 μg of 6 base N1A, N1B, N2A, N2B, N3A, N3B, N4A, N4B, N5A, N5B, N6A, N6B, N7A or N7B polynucleotides. Production of IFN-gamma was determined in 100 μl of culture supernatant using a commercial ELISA (BioSource) after 48 hours of incubation. Results are expressed as the "fold" (x) increase in IFN-gamma production by treated DC compared to control cells.

TABLE 5

IFN-gamma production by DC
(fold increase compared to untreated DC)

| | DC isolated from individual | | |
|---|---|---|---|
| SEQUENCE | A | B | C |
| N1A | 0.8 | 1.0 | 1.0 |
| N1B | 0.9 | 1.0 | 1.0 |
| N2A | 1.0 | 1.1 | 1.0 |
| N2B | 1.2 | 1.2 | 1.0 |
| N3A | 1.0 | 1.0 | 1.0 |
| N3B | 2.0 | 4.5 | 1.3 |
| N4A | 1.0 | n.d. | 1.0 |
| N4B | 1.0 | n.d. | 1.0 |
| N5A | 1.1 | 1.1 | 1.0 |
| N5B | 3.5 | 5.0 | 1.5 |
| N6A | 1.0 | 1.0 | 1.0 |
| N6B | 1.1 | 1.0 | 1.1 |
| N7A | 1.0 | n.d. | 1.0 |
| N7B | 1.1 | n.d. | 1.1 |

As shown in Table 5, polynucleotide N3B and polynucleotide N5B induced the production of IFN-gamma in cells of the three individuals tested.

EXAMPLE 7

Induction of IL-12 by Sequences Plus GM-CSF

DC from the individual B were seeded in 1.0 ml at $1.0 \times 10^5$ cells/ml in 6-well flat-bottomed tissue culture plates for 48 hours with 500 units of human recombinant GM-CSF (Clonetics) and 100 µg of 6 base polynucleotide N1A or polynucleotide N7A. Production of IL-12 was determined in 100 µl of culture supernatant using a commercial ELISA (BioSource) after 48 hours of incubation. Results are expressed as the "fold" (x) increase in IL-12 production by treated DC compared to control cells in absence or presence of recombinant GM-CSF.

TABLE 6

IL-12 production by DC from the individual B
in presence of GM-CSF (fold increase compared
to untreated DC)

| | IL-12 | |
|---|---|---|
| SEQUENCE | w/o | +GM-CSF |
| untreated | 1.0 | 1.0 |
| N1A | 14.7 | 15.3 |
| N7A | 9.6 | 11.7 |

As shown in Table 6, synergy was observed between GM-CSF and polynucleotide N1A or polynucleotide N7A for the production of IL-12 by DC.

EXAMPLE 8

Increase of CD40 Levels at the DC Cell Surface

DC from individuals B and C were seeded in 1.0 ml at $1.0 \times 10^5$ cells/ml in 6-well flat-bottomed tissue culture plates for 48 hours with 100 µg of 6 base N1A, N1B, N2A, N2B, N3A, N3B, N4A, N4B, N5A, N5B, N6A, N6B, N7A or N7B polynucleotides. The level of CD40 at the cell surface was determined after 48 hours of incubation by flow cytometry (FACSCalibur system) using a FITC-conjugated monoclonal antibody directed to CD40 and analyzed by CELLQuest Pro (all from Becton Dickinson). Results are expressed as the percentage of $CD40^{hi}$ DC following treatment. The term "$CD40^{hi}$" refers to a population of cells identified by flow cytometry as having higher than baseline expression of CD40.

TABLE 7

The percentage of $CD40^{hi}$ DC following treatment

| | DC from individuals | |
|---|---|---|
| SEQUENCE | B | C |
| untreated | 8 | 8 |
| N1A | 21 | 24** |
| N1B | 31** | 18 |
| N2A | 27** | 17 |
| N2B | 22 | 37** |
| N3A | 36** | 20 |
| N3B | 33** | 14 |
| N4A | n.d. | 16 |
| N4B | n.d. | 16 |
| N5A | 40** | 30** |
| N5B | 21 | 15 |
| N6A | 35** | 15 |
| N6B | 28** | 15 |
| N7A | n.d. | 23 |
| N7B | n.d. | 18 |

As shown in Table 7, a number of sequences have the ability to significantly up-regulate the expression of CD40 at the cell surface of DC.
**$p < 0.001$ Kolmogorov-Smirnov ($D > 0.20$).

EXAMPLE 9

Increase of CD80 Levels at the DC Cell Surface

DC from individuals B and C were seeded in 1.0 ml at $1.0 \times 10^5$ cells/ml in 6-well flat-bottomed tissue culture plates for 48 hours with 100 µg of 6 base N1A, N1B, N2A, N2B, N3A, N3B, N4A, N4B, N5A, N5B, N6A, N6B, N7A or N7B polynucleotides. The level of CD80 at the cell surface was determined after 48 hours of incubation by flow cytometry using a FITC-conjugated monoclonal antibody directed to CD80 (Serotec, Oxford, U.K.) and analyzed by CELLQuest. Results are expressed as the percentage of $CD80^{hi}$ DC following treatment.

TABLE 8

The percentage of $CD80^{hi}$ DC following treatment

| | DC from individual | |
|---|---|---|
| SEQUENCE | B | C |
| untreated | 7 | 7 |
| N1A | 45** | 41** |
| N1B | 11 | 13 |
| N2A | 25** | 18 |
| N2B | 7 | 8 |
| N3A | 12 | 18 |
| N3B | 5 | 3 |
| N4A | 11 | 21** |
| N4B | 9 | 13 |
| N5A | 18 | 14 |
| N5B | 3 | 10 |
| N6A | 15 | 17 |
| N6B | 4 | 4 |
| N7A | 23** | 22** |
| N7B | 5 | 5 |

TABLE 8-continued

The percentage of CD80$^{hi}$ DC following treatment

| | DC from individual | |
|---|---|---|
| SEQUENCE | B | C |

As shown in Table 8, a number of sequences significantly up regulated expression of CD80 at the cell surface of DC.
**p < 0.001 Kolmogorov-Smirnov (D > 0.20).

EXAMPLE 10

Increase of CD86 Levels at the DC Cell Surface

DC from individuals B and C were seeded in 1.0 ml at 1.0×10$^5$ cells/ml in 6-well flat-bottomed tissue culture plates for 48 hours with 100 μg of 6 base N1A, N1B, N2A, N2B, N3A, N3B, N4A, N4B, N5A, N5B, N6A, N6B, N7A or N7B polynucleotides. The level of CD86 at the cell surface was determined after 48 hours of incubation by flow cytometry using a PE-conjugated monoclonal antibody directed to CD86 (Serotec) and analyzed by CELLQuest Pro. Results are expressed as the percentage of CD86$^{hi}$ DC following treatment.

TABLE 9

The percentage of CD86$^{hi}$ DC following treatment.

| | DC from individual | |
|---|---|---|
| SEQUENCE | B | C |
| untreated | 14 | 16 |
| N1A | 10 | 14 |
| N1B | 19 | 27 |
| N2A | 16 | 26 |
| N2B | 31** | 53** |
| N3A | 16 | 37** |
| N3B | 30** | 39** |
| N4A | n.d. | 23 |
| N4B | n.d. | 32 |
| N5A | 20 | 16 |
| N5B | 26** | 31** |
| N6A | 24** | 18 |
| N6B | 15 | 33 |
| N7A | n.d. | 34 |
| N7B | n.d. | 34 |

As shown in Table 10, a number of sequences significantly up-regulated the expression of CD86 at the cell surface of DC.
**p < 0.001 Kolmogorov-Smirnov (D > 0.20).

EXAMPLE 11

Increase of MHC-II Levels at the DC Cell Surface

DC from individual B were seeded in 1.0 ml at 1.0×10$^5$ cells/ml in 6-well flat-bottomed tissue culture plates for 48 hours with 100 μg of 6 base N1A, N1B, N2A, N2B, N3A, N3B, N5A, N5B, N6A, N6B, N7A or N7B polynucleotides. The level of MHC II at the cell surface was determined after 48 hours of incubation by flow cytometry using a FITC-conjugated monoclonal antibody directed to MHC II (Serotec) and analyzed by CELLQuest Pro. Results are expressed as the percentage of MHC II$^{hi}$ DC following treatment.

TABLE 10

The percentage of MHC-II$^{hi}$ DC following treatment.

| SEQUENCE | DC from individual B |
|---|---|
| untreated | 22 |
| N1A | 32** |
| N1B | 7 |
| N2A | 42** |
| N2B | 30 |
| N3A | 23 |
| N3B | 25 |
| N5A | 19 |
| N5B | 18 |
| N6A | 25 |
| N6B | 27 |
| N7A | 21 |
| N7B | 31** |

As shown in Table 10, polynucleotides N1A, N2A and N7B significantly up regulated the expression of MHC II at the cell surface of DC.
**p < 0.001 Kolmogorov-Smirnov (D > 0.12).

EXAMPLE 12

Decrease of OX-2 Levels at the DC Cell Surface

DC from individual A were seeded in 1.0 ml at 1.0×10$^5$ cells/ml in 6-well flat-bottomed tissue culture plates for 48 hours with 1, 10 or 100 μg of 6 base N3A or N6A polynucleotides. The level of OX-2 at the cell surface was determined after 48 hours of incubation by flow cytometry using a FITC-conjugated monoclonal antibody directed to OX-2 (BioSPARK, Greenwich, Conn., USA) and analyzed by CELLQuest Pro. OX-2, a DC surface antigen, has been found to inhibit the stimulation of Th1 cytokine production and to provide a tolarizing signal to immune cells (Gorczynski et al., J. Immunol. 1999 162:774-781). Results are expressed as the percentage of OX-2$^{hi}$ DC following treatment.

TABLE 11

The percentage of OX-2$^{hi}$ DC following treatment.

| SEQUENCE | OX-2 percentage |
|---|---|
| untreated | 66 |
| N3A 1.0 μg | 61 |
| N3A 10.0 μg | 51** |
| N3A 100.0 μg | 51** |
| N6A 1.0 μg | 64 |
| N6A 10.0 μg | 62 |
| N6A 100.0 μg | 64 |

As shown in Table 12, polynucleotide N3A significantly down regulated the expression of OX-2 at the cell surface of DC.
**p < 0.001 Kolmogorov-Smirnov (D > 0.20).

EXAMPLE 13

Increase of Endocytosis by DC

DC from individual B were seeded in 1.0 ml at 1.0×10$^5$ cells/ml in 6-well flat-bottomed tissue culture plates for 24 hours with 1 mg/ml of FITC-dextran (20 kDa; Sigma-Aldrich) in the absence or presence of 100 μg of 6 base N2A, N2B, N3A, N3B, N5A, N5B, and N6B polynucleotides at 4° C. (control cell surface binding of FITC-dextran) and 37° C. (to assess endocytosis). Cells were washed three times with ice-cold phosphate buffered saline and analyzed by flow cytometry using CELLQuest Pro. Results are expressed as relative endocytic rate (normalized Δ Mean Fluorescence Value (Δ MFV)). Δ MFV=MFV of DC exposed to FITC-dextran at 37° C.−MFV of DC exposed to FITC-dextran at 4° C. Δ MFV=(ΔMFVsequence/ΔMFVcontrol)×100.

TABLE 12

The relative endocytic rate of DC following treatment

| SEQUENCE | Relative endocytic rate (normalized Δ MFV) DC from individual B |
|---|---|
| untreated (control) | 100 |
| N2A | 334 |
| N2B | 148 |
| N3A | 156 |
| N3B | 211 |
| N5A | 209 |
| N5B | 151 |
| N6B | 23 |

As shown in Table 12, N2A, N2B, N3A, N5A and N5B polynucleotides increased the endocytic rate of DC.

EXAMPLE 14

Cancer Vaccination with Antigen-Pulsed DC

DC isolated from C57BL/6 mice are loaded in vitro with tumor cell lysate from melanoma B-16 cells. N1A, N1B, N2A, N2B, N3A, N3B, N4A, N4B, N5A, N5B, N6A, N6B, N7A or N7B polynucleotides are included during antigen pulsing. Seventy-five C57BL/6 mice are injected subcutaneously with about $2 \times 10^6$ B-16 melanoma cells.

Seven days after tumor inoculation, mice are divided into 15 groups of 5 mice each. Group 1 mice are vaccinated with $2 \times 10^4$ B-16 tumor lysate-pulsed DC; Group 2 mice are vaccinated with $2 \times 10^4$ B-16 tumor lysate-pulsed DC+100 µg of N1A polynucleotide; Group 3 mice are vaccinated with $2 \times 10^4$ B-16 tumor lysate-pulsed DC+100 µg of N1B polynucleotide; Group 4 mice are vaccinated with $2 \times 10^4$ B-16 tumor lysate-pulsed DC+100 µg+N2A polynucleotide; Group 5 mice are vaccinated with $2 \times 10^4$ B-16 tumor lysate-pulsed DC+100 µg of N2B polynucleotide; Group 6 mice are vaccinated with $2 \times 10^4$ B-16 tumor lysate-pulsed DC+100 µg of N3A polynucleotide; Group 7 mice are vaccinated with $2 \times 10^4$ B-16 tumor lysate-pulsed DC+100 µg of N3B polynucleotide; Group 8 mice are vaccinated with $2 \times 10^4$ B-16 tumor lysate-pulsed DC+100 µg of N4A polynucleotide; Group 9 mice are vaccinated with $2 \times 10^4$ B-16 tumor lysate-pulsed DC+100 µg of N4B polynucleotide; Group 10 mice are vaccinated with $2 \times 10^4$ B-16 tumor lysate-pulsed DC+100 µg of N5A polynucleotide; Group 11 mice are vaccinated with $2 \times 10^4$ B-16 tumor lysate-pulsed DC+100 µg of N5B polynucleotide; Group 12 mice are vaccinated with $2 \times 10^4$ B-16 tumor lysate-pulsed DC+100 µg of N6A polynucleotide; Group 13 mice are vaccinated with $2 \times 10^4$ B-16 tumor lysate-pulsed DC+100 µg of N6B polynucleotide; Group 14 mice are vaccinated with $2 \times 10^4$ B-16 tumor lysate-pulsed DC+100 µg of N7A polynucleotide; and Group 15 mice are vaccinated with $2 \times 10$ B-16 tumor lysate-pulsed DC+100 µg of N7B polynucleotide.

One week later the previously described vaccinations are repeated. After 2 weeks, the volume and weight of the tumors were analyzed. Group 2-15 mice have less tumor mass than Group 1 mice. Specific cytotoxic T lymphocytes (CTL) directed to B-16 antigens are analyzed by IFN-gamma ELISPOT using peripheral blood mononuclear cells derived from mice before and after injection of tumor lysate-pulsed DC and polynucleotide. The frequency of CTL directed to B-16 is higher in Group 2-15 mice than in Group 1 mice.

EXAMPLE 15

Vaccination with *Bordatella pertussis*-pulsed DC

DC isolated from C57BL/6 mice are loaded in vitro with $10^7$ heat-killed *Bordatella pertussis*. N1A, N1B, N2A, N2B, N3A, N3B, N4A, N4B, N5A, N5B, N6A, N6B, N7A or N7B polynucleotides are included during antigen pulsing. Seventy C57BL/6 mice are divided into 15 groups of 5 mice. Group 1 mice are vaccinated with $10^7$ heat-killed *Bordatella pertussis*-pulsed DC; Group 2 mice are vaccinated with $10^7$ heat-killed *Bordatella pertussis*-pulsed DC+100 µg of N1A polynucleotide; Group 3 mice are vaccinated with $10^7$ heat-killed *Bordatella pertussis*-pulsed DC+100 µg of N1B polynucleotide; Group 4 mice are vaccinated with $10^7$ heat-killed *Bordatella pertussis*-pulsed DC+100 µg+N2A polynucleotide; Group 5 mice are vaccinated with $10^7$ heat-killed *Bordatella pertussis*-pulsed DC+100 µg of N2B polynucleotide; Group 6 mice are vaccinated with $10^7$ heat-killed *Bordatella pertussis*-pulsed DC+100 µl of N3A polynucleotide; Group 7 mice are vaccinated with $10^7$ heat-killed *Bordatella pertussis*-pulsed DC+100 µg of N3B polynucleotide; Group 8 mice are vaccinated with $10^7$ heat-killed *Bordatella pertussis*-pulsed DC+100 µg of N4A polynucleotide; Group 9 mice are vaccinated with $10^7$ heat-killed *Bordatella pertussis*-pulsed DC+100 µg of N4B polynucleotide; Group 10 mice are vaccinated $10^7$ heat-killed *Bordatella pertussis*-pulsed DC+100 µg of N5A polynucleotide; Group 11 mice are vaccinated with $10^7$ heat-killed *Bordatella pertussis*-pulsed DC+100 µg of N5B polynucleotide; Group 12 mice are vaccinated $10^7$ heat-killed *Bordatella pertussis*-pulsed DC+100 µg of N6A polynucleotide; Group 13 mice are vaccinated with $10^7$ heat-killed *Bordatella pertussis*-pulsed DC+100 µg of N6B polynucleotide; Group 14 mice are vaccinated with $10^7$ heat-killed *Bordatella pertussis*-pulsed DC+100 µg of N7A polynucleotide; and Group 15 mice are vaccinated with $10^7$ heat-killed *Bordatella pertussis*-pulsed DC+100 µg of N7B polynucleotide.

The above-described vaccinations are repeated two times at weekly intervals. Two weeks after the last administration of DC, the mice are challenged with $5 \times 10^6$ *Bordatella pertussis* (intranasal administration). The animals are killed after challenge and assayed for *Bortadella pertussis*-specific IgG levels in serum, bacterial load in the lungs, and *Bortadella pertussis*-specific antibody-secreting cells in the lungs. Group 2-15 mice show higher level of *Bortadella pertussis*-specific IgG than Group 1 mice. Group 2-15 mice show less *Bortadella pertussis* in the lung than Group 1 mice. Group 2-15 mice show higher level of *Bortadella pertussis*-specific antibody-secreting cells in the lung.

EXAMPLE 16

Vaccination with Hepatitis Surface Antigen

Immunization with recombinant hepatitis B surface antigen (HbsAg; Cortex Biochemical, San Leandro, Calif., USA) combined with aluminum hydroxide (Alum; Super-Fos Biosector, Vedback, Denmark) and/or with N3A, N6A or N6B polynucleotides, was conducted on 6-8 week old female BALB/C mice (Charles River, St-Constant, Qc, Canada). Each mouse (5 mice per group) received a single intramuscular injection into the tibialis muscle of a solution containing: Saline (Group 1), HbsAg 1 μg (Group 2), HbsAg 1 μg+Alum 10 μg (Group 3), HbsAg 1 μg+Alum 10 μg+N3A 10 μg (Group 4), HbsAg 1 μg+Alum 10 μg+N3A 100 μg (Group 5), HbsAg 1 μg+Alum 10 μg+N3B10 μg (Group 6), HbsAg 1 μg+Alum 10 μg+N3B100 μg (Group 7), HbsAg 1 μg+Alum 10 μg+N6A 10 μg (Group 8), HbsAg 1 μg+Alum 10 μg+N6A 100 μg (Group 9), HbsAg 1 μg+Alum 10 μg+N6B 10 μg (Group 10) and HbsAg 1 μg+Alum 10 μg+N6B 100 μg (Group 11) in a total volume of 50 μl at day 0 and day 21. Plasma was recovered at day 31.

Antibodies specific to HbsAg were detected and quantified by end-point dilution assay ELISA. Briefly, a solid phase of HbsAg protein (0.1 μg per well, overnight at 4° C.) was used to capture anti-HbsAg in the plasma (1 hour at 37° C.), which were then detected with horseradish peroxidase-conjugated goat anti-mouse IgG (total), IgG1 and IgG2a following the instructions of the manufacturer (Clonetyping system, Southern Biotechnology Inc., Birmingham, Ala., USA). End-point titers were defined as the highest plasma dilution that resulted in an absorbance value (OD 450) two times greater than that of the control (Group 1). Data are expressed in Table 13 as the mean±SD of 5 mice per group.

TABLE 13

End-point titers for mice immunized with HbsAg

| | End-point titers | | |
|---|---|---|---|
| Group | IgG total mean ± SD (range) | IgG1 mean ± SD (range) | IgG2a mean ± SD (range) |
| 1 | 50 ± 10 (38-65) | 728 ± 99 (625-840) | 67 ± 39 (0-95) |
| 2 | 214 ± 134 (80-375) | 1516 ± 537 (880-2300) | 211 ± 127 (93-420) |
| 3 | 800 ± 248 (550-1200) | 4400 ± 1042 (3500-5800) | 259 ± 187 (120-580) |
| 4 | 849 ± 386 (520-1500) | 9300 ± 3365 (4500-13500) | 272 ± 255 (90-715) |
| 5 | 1985 ± 1748 (800-4800) | 13320 ± 12993 (4800-35000) | 860 ± 719 (150-1850) |
| 6 | 287 ± 142 (150-520) | 3460 ± 1680 (1550-4700) | 120 ± 26 (90-155) |
| 7 | 437 ± 305 (100-750) | 4460 ± 1884 (1400-6200) | 204 ± 129 (82-420) |
| 8 | 439 ± 705 (95-1700) | 2010 ± 2187 (750-5900) | 250 ± 257 (90-700) |
| 9 | 1185 ± 607 (525-1900) | 6420 ± 2528 (4000-9800) | 291 ± 154 (90-440) |
| 10 | 551 ± 309 (250-1000) | 2880 ± 1126 (1900-4700) | 187 ± 46 (135-260) |
| 11 | 660 ± 364 (520-1500) | 3560 ± 1210 (1700-5000) | 205 ± 76 (140-320) |

As shown in Table 13, N3A (Group 4: HbsAg 1 μg + Alum 10 μg + N3A 10 μg and Group 5: HbsAg 1 μg + Alum 10 μg + N3A 100 μg) and N6A (Group 9: HbsAg 1 μg + Alum 10 μg + N6A 100 μg) have the ability to significantly stimulate the immune response against HbsAg by increasing the titer of IgG, IgG1 and IgG2a against HbsAg.

EXAMPLE 17

Oral Vaccination with Hepatitis Surface Antigen

Immunization with recombinant hepatitis B surface antigen combined with N6A or N6B polynucleotide was conducted on 6-8 week old female BALB/C mice (Charles River, St-Constant, Qc, Canada). Each mouse (5 mice per group) has received orally a solution containing: Saline (Group 1), HbsAg 10 μg (Group 2), HbsAg 10 μg+N6A 1 μg (Group 3), HbsAg 10 μg+N6A 10 μg (Group 4), HbsAg 10 μg+N6A 100 μg (Group 5), HbsAg 10 μg+N6B 1 μg (Group 6), HbsAg 10 μg+N6B 10 μg (Group 7) and HbsAg 10 μg+N6B 100 μg (Group 8) in a total volume of 50 μl at day 0, 7 and day 14. Plasma and gut washes were recovered at day 21. Gut washes (for IgA determination) were obtained by gently pipetting 0.2 ml of PBS containing protease inhibitors (10 μg pepstatin, 10 μg leupeptin, 10 μg antipain and 50 μg benzamidine).

Antibodies specific to HbsAg were detected and quantified by ELISA. Briefly, a solid phase of HbsAg protein (1.0 μg per well, overnight at 4° C.) was used to capture anti-HbsAg in the plasma or in the gut washes (1 hour at 37° C.), which were then detected with horseradish peroxidase-conjugated goat anti-mouse IgA (for gut washes) and goat anti-mouse total IgG (for plasma) following the instructions of the manufacturer (Clonetyping system, Southern Biotechnology Inc.). Data are expressed in Table 14 in OD (450 nm) as the mean±SD of 5 mice per group. ODs for IgA are obtained following 1:2 gut washes dilution while total IgG are obtained following 1:16 serum dilution.

TABLE 14

OD (450 nm) for mice orally immunized with HbsAg

| | OD (optical density at 450 nm) | |
|---|---|---|
| Group | IgA total at 1:2 dilution mean ± SD (range) | Total IgG at 1:32 dilution mean ± SD (range) |
| | (0.118-0.453) | (0.060-0.185) |
| 2 | 0.452 ± 0.119 (0.290-0.558) | 0.124 ± 0.055 (0.060-0.191) |
| 3 | 0.662 ± 0.166 (0.459-0.790) | 0.138 ± 0.055 (0.080-0.254) |
| 4 | 0.853 ± 0.543 (0.399-1.906) | 0.141 ± 0.044 (0.090-0.213) |
| 5 | 0.650 ± 0.276 (0.440-1.170) | 0.121 ± 0.055 (0.064-0.215) |
| 6 | 0.549 ± 0.242 (0.323-0.865) | 0.104 ± 0.030 (0.072-0.161) |
| 7 | 0.333 ± 0.156 (0.171-0.628) | 0.225 ± 0.135 (0.103-0.414) |
| 8 | 0.492 ± 0.074 (0.387-0.601) | 0.120 ± 0.057 (0.063-0.229) |

As shown in Table 14, N6A (Group 3: HbsAg 10 μg + N6A 1 μg; Group 4: HbsAg 10 μg + N6A 10 μg and Group 5: HbsAg 10 μg + N6A 100 μg) and N6B (Group 8: HbsAg 10 μg + N6B 100 μg) significantly stimulated the immune response against HbsAg following oral administration.

All patents, publications and abstracts cited above are incorporated herein by reference in their entirety. It should be understood that the foregoing relates only to preferred embodiments of the present invention and that numerous modifications or alterations may be made therein without departing from the spirit and the scope of the present invention as defined in the following claims.

We claim:

1. A method of stimulating an immune response in an animal or human comprising administering to the animal or the human a composition comprising a 3'-OH, 5'-OH polynucleotide sequence and a pharmaceutically acceptable carrier: wherein,
   a) the 3'-OH, 5'-OH polynucleotide sequence is six bases of which at least 50% are guanine and wherein a guanine is located at the 5' end of the six bases; and,
   b) the composition stimulates the immune response in the animal or human,
   wherein the immune response comprises one or more responses selected from the group consisting of an increase in cell size, an increase in granularity, an increase in CD40, CD80, CD86 or MHC II cell surface expression, a decrease in OX-2 cell surface expression, a systemic immune response, a mucosal immune response and an increase in endocytosis.

2. The method of claim 1, wherein the polynucleotide sequence is 5'GTGTGT3' (SEQ ID NO: 1), 5'GGTGGG3' (SEQ ID NO: 2), 5'GGGTGG3' (SEQ ID NO: 3), 5'GGGCGG3' (SEQ ID NO: 7), 5'GGGAGG3' (SEQ ID NO: 6), 5'GGGGGG3' (SEQ ID NO: 5) or 5'GGCCGG3' (SEQ ID NO: 4).

3. The method of claim 1, wherein the polynucleotide sequence is 5'GGGTGG3' (SEQ ID NO: 3) or 5'GGGAGG3' (SEQ ID NO: 6).

4. The method of claim 1, wherein the polynucleotide sequence comprises a phosphodiester backbone.

5. The method of claim 1, wherein the polynucleotide sequence comprises a phosphorothioate backbone.

6. The method of claim 1, wherein administering the composition is by a local administration route selected from the group consisting of a subcutaneous, intramuscular, intratissular, intrathecal and transdermal route.

7. The method of claim 1, wherein administering the composition is by a mucosal administration route selected from the group consisting of an intravesical, ocular, oral, nasal, rectal and vaginal route.

8. The method of claim 1, wherein the polynucleotide is administered in a sustained release device.

9. The method of claim 1, further comprising administering an antigen to the animal or human, and wherein the immune response is antigen-specific.

10. The method of claim 1, further comprising administering a therapeutic modality.

11. The method of claim 10, wherein the therapeutic modality is a chemotherapeutic agent, an antimicrobial agent or an antiviral agent.

12. The method of claim 11, wherein the chemotherapeutic agent is an anti-metabolite, a DNA damaging agent, a microtubule destabilizing agent, a microtubule stabilizing agent, an actin depolymerizing agent, a growth inhibiting agent, a topoisomerase inhibiting agent, a HMG-CoA inhibiting agent, a purine inhibiting agent, a pyrimidine inhibiting agent, a metalloproteinase inhibiting agent, a CDK inhibiting agent, an angiogenesis inhibiting agent or a differentiation enhancing agent.

13. The method of claim 1, further comprising administering an immunomodulatory agent.

14. A method of treating a disease in an animal or human comprising administering to the animal or the human a composition comprising an isolated 3'-OH, 5'-OH polynucleotide sequence and a pharmaceutically acceptable carrier: wherein,
   a) the isolated 3'-OH, 5'-OH polynucleotide sequence comprises six bases of which at least 50% are guanine and wherein a guanine is located at the 5' end of the six bases; and;
   b) the composition treats the disease in the animal or the human,
   wherein the disease is melanoma.

15. The method of claim 1, wherein the pharmaceutically acceptable carrier is a liquid carrier, a solid carrier or a combination thereof.

16. The method of claim 15, wherein the liquid carrier is water, saline, a physiologically acceptable buffer, an aqueous suspension, an oil emulsion, a water-in-oil emulsion, a water-in-oil-in-water emulsion, a site-specific emulsion, a long-residence emulsion, a sticky emulsion, a microemulsion or a nanoemulsion.

17. The method of claim 15, wherein the solid carrier is a chemical carrier, a biological carrier, a particle, a microparticle, a nanoparticle, a microsphere, a nanosphere, a minipump, a bacterial cell wall extract, a biodegradable or non-biodegradable natural or synthetic polymer that allow for sustained release of the polynucleotide composition.

18. The method of claim 1, when the composition further comprises a diluent, excipient or carrier, wherein the diluent, excipient or carrier is a filler, an extender, a binding agent, a moisturizing agent, a disintegrating agent, an agent for retarding dissolution, a resorption accelerator, a surface active agent, an adsorptive carrier, an emulsifier, a preservative, a sweetener, a stabilizer, a coloring agent, a perfuming agent, a flavoring agent, a lubricant, a solid polyethyl glycol or a mixture thereof.

19. The method of claim 1, wherein the administering is oral, anal, rectal, as a suppository, topical, parenteral, nasal, aerosol, inhalation, subcutaneous, transdermal, intradermal, subdermal, intramuscular, intraperitoneal, intrathecal, intraarterial, intravenous, intratissular, intrauterine, vaginal, into a body cavity, surgical administration at the location of a tumor or internal injury, directly into a tumor, into the lumen or parenchyma of an organ, into bone marrow, into the mucosal surface of the gastrointestinal, reproductive, urinary or genitourinary system.

20. The method of claim 1, wherein a volume of the composition administered per dose is about 0.001 to 100 ml per dose.

21. The method of claim 1, wherein a volume of the composition administered per dose is about 0.01 to 50 ml per dose.

22. The method of claim 1, wherein a volume of the composition administered per dose is about 0.1 to 30 ml per dose.

23. The method of claim 1, wherein an amount of composition administered per dose is about 0.0001 to 100 mg per kg body weight.

24. The method of claim 1, wherein an amount of composition administered per dose is about 0.001 to 10 mg per kg body weight.

25. The method of claim 1, wherein an amount of composition administered per dose is about 0.01 to 5 mg per kg body weight.

* * * * *